United States Patent [19]

Hirota et al.

[11] 4,106,993

[45] Aug. 15, 1978

[54] METHOD FOR PRESERVATION OF AQUEOUS GLUCOSE ISOMERASE SOLUTION

[75] Inventors: Tetsuya Hirota, Fujisawa; Tadashi Hishida, Tokyo; Akira Kamata, Yokohama; Isao Nakazawa, Kawasaki; Hiroshi Takamisawa, Yokohama, all of Japan

[73] Assignee: Mitsubishi Chemical Industries Limited, Tokyo, Japan

[21] Appl. No.: 777,685

[22] Filed: Mar. 15, 1977

[30] Foreign Application Priority Data

Mar. 17, 1976 [JP] Japan .................................. 51-28963

[51] Int. Cl.² .......................... C07G 7/02; C12K 1/00
[52] U.S. Cl. ...................................................... 195/65
[58] Field of Search .......................... 195/65, 66 R, 68

[56] References Cited
U.S. PATENT DOCUMENTS

| | | | |
|---|---|---|---|
| 3,826,714 | 7/1974 | Suekane et al. .................... | 195/31 F |
| 3,933,538 | 1/1976 | Dworschack et al. ................ | 195/68 |
| 3,941,655 | 3/1976 | Heady et al. ....................... | 195/31 F |

OTHER PUBLICATIONS

Kasumi et al., Journal of Fermentation Technology vol. 52, No. 5, pp. 321–327, (1974).
Takasaki et al., Fermentation Advances, 1969 edited by D. Perlman, pp. 561–589.

*Primary Examiner*—Lionel M. Shapiro
*Attorney, Agent, or Firm*—Oblon, Fisher, Spivak, McClelland & Maier

[57] ABSTRACT

A method for preservation of an aqueous glucose isomerase solution is disclosed in which an aqueous glucose isomerase solution is mixed with a an alkaline material to adjust its pH value within a range of from 9 to 12 whereby the aqueous solution can be stored at room temperature for a period not less than three days without microbial contamination, putrefaction, denaturation and deactivation of the glucose isomerase.

10 Claims, 2 Drawing Figures

\* MICROBIAL CONTAMINATION WAS OBSERVED

* MICROBIAL CONTAMINATION WAS OBSERVED

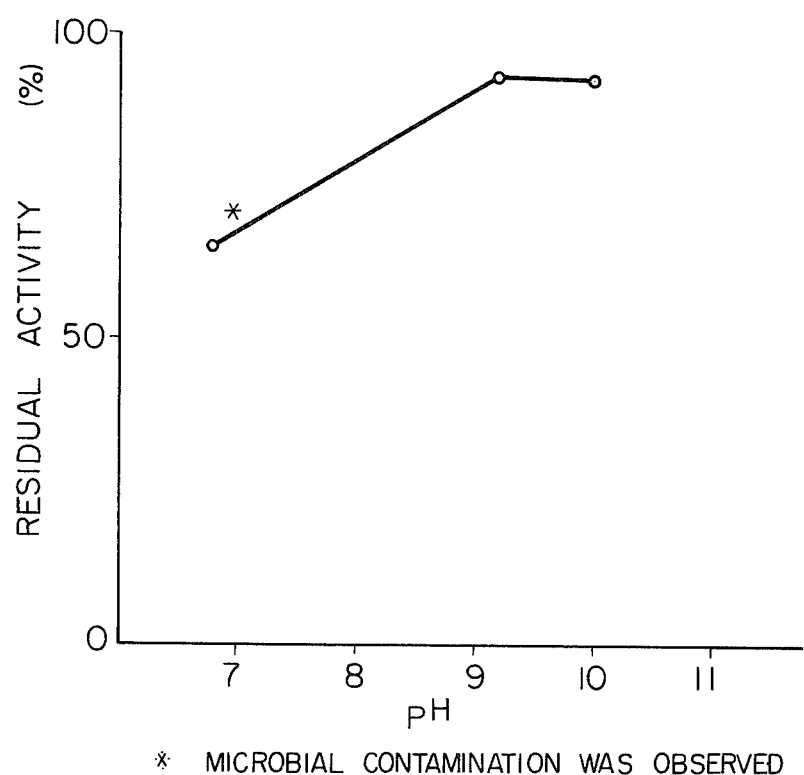

METHOD FOR PRESERVATION OF AQUEOUS GLUCOSE ISOMERASE SOLUTION

This invention relates to a method for preservation of an aqueous glucose isomerase solution, and more particularly to a method for preservation of an aqueous glucose isomerase solution at room temperature for a long time in good state.

Glucose isomerase is an enzyme capable of converting glucose into fructose and vice versa and is used for the commercial production of fructose from glucose.

Glucose isomerase is found within the cells of various microorganisms, for example, actinomycetes, and, heretofore, the cells of microorganisms, especially the cells of the strain of streptomyces, have been utilized as sources of glucose isomerase.

In recent years, there has been the trend of converting glucose isomerase extracted from microorganism cells into insolubilized or immobilized form. Since such insolubilized glucose isomerase possesses a long life time as used in the conversion of glucose and tends to reduce the coloration of the product fructose, insolubilized glucose isomerase becomes commercially important.

In general, insolubilized glucose isomerase is prepared by extracting glucose isomerase from microorganism cells in water by various treatments, for example, ultrasonic treatment, autolysis, bacteriolytic enzyme treatment, high pressure breaking and mechanical grinding, and subjecting the aqueous glucose isomerase extract to insolubilization, for example, covalent bonding, ion binding, adsorption, cross-linking or inclusion, after subjecting the aqueous extract to purification if necessary.

Glucose isomerase is unstable in an aqueous solution as in the case of various enzymes. For example, if an aqueous glucose isomerase extract is allowed to stand at room temperature, the extract is microbially contaminated within about one day to cause putrefaction and to lower its activity.

Thus, it is common to store an aqueous glucose isomerase extract at lower temperature, for example, from −20° to 5° C, but this is not suitable for long-time storage and shipment, especially in large lots due to the requirement of expensive equipment for maintaining such low temperature. Further, at a temperature of from 0° to 10° C, microbial contamination cannot be prevented satisfactorily. We have found that an aqueous glucose isomerase extract adjusted to a pH within the range of from 9 to 12 by addition of an alkaline material is stable at room temperature for a long time, and this invention has been accomplished on the basis of this knowledge.

The aqueous glucose isomerase solution to which this invention is applied is prepared by subjecting a glucose isomerase-producing microorganism, such as bacteria belonging to *Pseudomonas, Bacillus, Lactobacillus* and *Brevibacterium*, actinomycete belonging to *Streptomyces* and yeast, to the above-mentioned various extraction treatments. Preferred source is actinomycete belonging to *Streptomyces*.

In general, an aqueous glucose isomerase extract has a pH value ranging from 6 to 8 and is most readily microbially contaminated at a pH of 8 which is the optimum pH value of the glucose isomerase. As the pH of the aqueous glucose isomerase extract rises over the optimum value, the activity lowers. In this respect, it is expected that the most effective way to store the aqueous glucose isomerase extract is at a pH of about 8. To our best knowledge, in contrast to the above expectation, it has now been found that, if an aqueous glucose isomerase solution is stored at a pH of above 9, especially from 10 to 11, the deactivation can be minimized.

Accordingly, an object of this invention is to provide a method for preservation of an aqueous glucose isomerase solution by adjusting the pH value within a range of from 9 to 12, preferably 10 to 11. Another object is to provide a method for preservation of an aqueous glucose isomerase solution comprising adding an alkaline material to the solution to maintain the pH within a range of from 9 to 12, preferably 10 to 11.

A further object is to provide a method for preservation of an aqueous glucose isomerase solution whereby to improve its stability on storage for a long time without microbial contamination. By "stability on storage" we mean the prevention of microbial contamination, putrefaction and denaturation, and the resistance to deactivation of an aqueous glucose isomerase solution during the storage.

The aqueous glucose isomerase solution extracted from microorganism cells as above is subjected to adjustment of the pH value to a range of from 9 to 12, preferably 10 to 11, by addition of an alkaline material. Examples of the alkaline material include, for example, sodium hydroxide, potassium hydroxide, magnesium hydroxide, and ammonium hydroxide; however, calcium hydroxide which hinders the enzymatic activity is to be excluded. The addition of such alkaline material may be effected at the start of storage. It is preferred that the alkaline material be added intermittently during the storage to maintain the pH value adjusted initially.

The temperature at which the aqueous glucose isomerase solution is stored is from the lyophilizing temperature to 80° C, preferably 0° to 70° C, from the viewpoint of the prevention of microbial contamination and easy handling.

This invention will be explained in detail by means of Examples. However, it should be understood that this invention is in no way limited by these Examples.

The preparation of a glucose isomerase extract, the measurement of activity and the measurement of contamination referred to in the Examples are as follows.

Preparation of Glucose Isomerase Extract

A suspension of 100g microorganism cell (in wet state) in 800 ml of demineralized water was mixed with 90 mg of egg white lysozyme crystal (after six times recrystallization) and agitation was continued at 50° C for four and a half hours. The mixture was centrifuged to obtain an aqueous glucose isomerase extract.

Measurement of Activity

A given amount of aqueous glucose isomerase solution was added to a mixture of 0.2 ml of a 1 M aqueous D-glucose, 0.2 ml of a 0.05 M $MgSO_4 \cdot 7H_2O$ and 0.2 ml of a 0.5 M phosphate buffer (pH 7.2) and the resulting mixture was diluted with demineralized water to 2ml. The mixture was maintained at 70° C for 60 minutes to effect isomerization. The reaction was stopped by addition of 2 ml of a 0.5 M aqueous $HClO_4$, and the amount of fructose produced was measured by the cystein-carbazole method. The activity was the amount of fructose produced with 1 ml of the aqueous glucose isomerase solution under the conditions mentioned above and was expressed by the unit "U" which represented the production of 1 mg of fructose.

Measurement of Contamination

An aqueous glucose isomerase solution stored for a given period was examined through a microscope and the degree of microbial contamination was evaluated on a four-degree scale; 0 represents little or no contamination and 3 represents extreme contamination.

BRIEF DESCRIPTION OF DRAWINGS

FIGS. 1 and 2 show residual activity of glucose isomerase after storage for one week at different pH.

EXAMPLE 1

Figure 1:
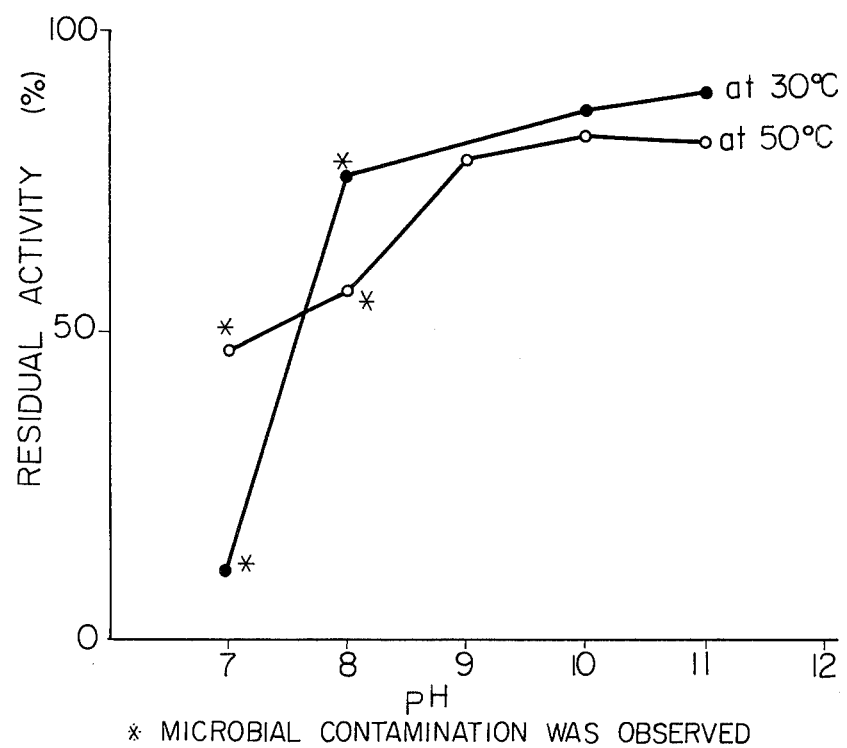

An aqueous glucose isomerase extract was prepared from "GLUCOSE ISOMERASE NAGASE" which was the lyophilized strain belonging to *Streptomyces phoechromogenes* and available from Nagase & Company Ltd., Osaka, Japan, the extract having a pH of 7.2 and an activity of 265 U/ml.

The aqueous extract was divided into six portions (each 50 ml) the pH value of which were adjusted to 6 and 7 with 1N hydrochloric acid and pH values of 8, 10, 11 and 12 with 1N aqueous sodium hydroxide, respectively, the last not being adjusted. From the each portion, each 5 ml samples were poured to test tubes which were then sealed air-tightly. The tubes were stored at the predetermined temperatures for predetermined periods given in Table 1. The microbial contamination and the activity were measured.

The results are given in Table 1.

Table 1

| Temp. (° C) | pH 0 day | pH 3 days | pH 7 days | Contamination 0 day | Contamination 3 days | Contamination 7 days | Activity (U/ml) 0 day | Activity (U/ml) 3 days | Activity (U/ml) 7 days |
|---|---|---|---|---|---|---|---|---|---|
| 4 | * 6.0 | 6.1 | 6.1 | 0 | 0 | 1 | 220 | 182 | 173 |
|   | * 7.2 | 7.1 | 7.0 | 0 | 1 | 1 | 265 | 200 | 184 |
|   | * 8.0 | 7.9 | 7.2 | 0 | 1 | 2 | 241 | 204 | 51 |
|   | 10.1 | 10.0 | 9.9 | 0 | 0 | 0 | 254 | 241 | 212 |
|   | 11.1 | 11.1 | 11.0 | 0 | 0 | 0 | 260 | 241 | 210 |
|   | 12.1 | 12.0 | 11.9 | 0 | 0 | 0 | 222 | 217 | 197 |
| 30 | * 6.0 | 6.9 | 7.1 | 0 | 3 | 3 | 220 | 150 | 74 |
|   | * 7.2 | 7.4 | 7.1 | 0 | 3 | 3 | 265 | 53 | 48 |
|   | * 8.0 | 6.5 | 8.2 | 0 | 3 | 3 | 241 | 188 | 170 |
|   | 10.1 | 7.1 | 7.2 | 0 | 1 | 3 | 254 | 250 | 205 |
|   | 11.1 | 10.3 | 9.6 | 0 | 0 | 0 | 264 | 241 | 221 |
|   | 12.1 | 11.6 | 11.0 | 0 | 0 | 0 | 222 | 220 | 215 |
| 50 | * 7.2 | 7.1 | 7.0 | 0 | 3 | 3 | 265 | 92 | 45 |
|   | * 8.0 | 7.3 | 7.0 | 0 | 3 | 3 | 241 | 191 | 143 |
|   | 10.1 | 9.2 | 8.0 | 0 | 0 | 0 | 254 | 252 | 201 |
|   | 11.1 | 10.2 | 9.9 | 0 | 0 | 0 | 264 | 236 | 200 |
|   | 12.1 | 10.9 | 10.5 | 0 | 0 | 0 | 222 | 200 | 170 |
| 70 | * 7.2 | 6.9 | 6.6 | 0 | 0 | 0 | 265 | 64 | 4 |
|   | * 8.0 | 7.4 | 6.6 | 0 | 0 | 1 | 241 | 143 | 21 |
|   | 10.1 | 8.7 | 7.8 | 0 | 0 | 0 | 254 | 144 | 143 |
|   | 11.1 | 9.7 | 8.9 | 0 | 0 | 0 | 264 | 189 | 135 |

* : For comparison purpose.

EXAMPLE 2

The strain of glucose isomerase-producing microorganism belonging to *Streptomyces albus* YT-No. 5 which had been deposited with American Type Culture Collection as ATCC-21132 was inoculated on 80 ml of a liquid medium containing 1% of polypeptone, 0.3% of $K_2HPO_4$, 0.1% of $MgSO_4 \cdot 7H_2O$ and 1% of xylose, by weight, and the cultivation was continued at pH 7 and 30° C for 30 hours.

Two milliliters of the cultivated medium was transferred to 10l of a medium containing 3% of corn bran, 2% of corn steep liquor, 0.1% of $MgSO_4 \cdot 7H_2O$ and 0.024% of $CoCl_2 \cdot 2H_2O$, by weight and the cultivation was continued at 30° C for 30 hours. The microorganism cells were collected by centrifuging and washed with water.

An aqueous glucose isomerase extract was obtained from the cells as mentioned hereinbefore, the extract having a pH of 7.3 and an activity of 240 U/ml. Following the procedures of Example 1, the extract was divided and the pH values were adjusted with 1N hydrochloric acid and 1N potassium hydroxide. The temperature at which test samples were stored were −20° C, 10° C and 30° C.

The results of the contamination and the activity measured are given in Table 2.

Table 2

| Temp. (° C) | pH 0 day | pH 3 days | pH 7 days | Contamination 0 day | Contamination 3 days | Contamination 7 days | Activity (U/ml) 0 day | Activity (U/ml) 3 days | Activity (U/ml) 7 days |
|---|---|---|---|---|---|---|---|---|---|
| ** (−20° C) | * 6.0 | 5.9 | 5.7 | 0 | 0 | 0 | 139 | 81 | 65 |
|   | * 7.3 | 7.3 | 7.0 | 0 | 0 | 0 | 240 | 222 | 198 |
|   | * 8.3 | 7.9 | 7.7 | 0 | 0 | 0 | 232 | 194 | 181 |
|   | 9.3 | 9.3 | 9.2 | 0 | 0 | 0 | 238 | 240 | 202 |
|   | 10.0 | 9.8 | 9.7 | 0 | 0 | 0 | 201 | 202 | 191 |
|   | 11.0 | 11.0 | 10.8 | 0 | 0 | 0 | 193 | 200 | 197 |
| 10 | * 7.3 | 7.2 | 7.3 | 0 | 1 | 2 | 240 | 233 | 143 |
|   | * 8.3 | 6.3 | 4.8 | 0 | 2 | 3 | 232 | 123 | 18 |
|   | 10.0 | 10.1 | 10.0 | 0 | 0 | 0 | 201 | 195 | 195 |
|   | 11.0 | 11.0 | 10.7 | 0 | 0 | 0 | 193 | 194 | 176 |
|   | 12.0 | 12.1 | 11.9 | 0 | 0 | 0 | 185 | 174 | 176 |

Table 2-continued

| Temp. (°C) | pH | | | Contamination | | | Activity (U/ml) | | |
|---|---|---|---|---|---|---|---|---|---|
| | 0 day | 3 days | 7 days | 0 day | 3 days | 7 days | 0 day | 3 days | 7 days |
| 30 | * 7.3 | 7.5 | 8.8 | 0 | 3 | 3 | 240 | 202 | 201 |
| | * 8.1 | 5.0 | 4.5 | 0 | 3 | 3 | 232 | 32 | 4 |
| | 11.0 | 9.8 | 7.2 | 0 | 0 | 1 | 193 | 180 | 171 |
| | 12.0 | 11.2 | 10.5 | 0 | 0 | 0 | 185 | 169 | 156 |

* For comparison purpose.
** Measured after thawing.

EXAMPLE 3

An aqueous glucose isomerase extract obtained as in Example 2 was stored at temperatures of 30° C and 50° C for seven days and its pH value was readjusted every 24 hours to the initial value. The residual activity was determined after storage for one week. The results are illustrated in FIG. 1.

The ranges within which the pH values varied on storage are given in Table 3.

Table 3

| Initial pH | Temp. | |
|---|---|---|
| | 30° C | 50° C |
| 7 | 5.8 – 7.3 | 6.8 – 7.2 |
| 8 | 7.7 – 8.3 | 7.5 – 8.5 |
| 9 | | 8.0 – 9.4 |
| 10 | 9.6 – 10.4 | 9.3 – 10.2 |
| 11 | 10.0 – 11.1 | 10.1 – 11.8 |

EXAMPLE 4

Each 3 ml samples of the aqueous glucose isomerase extract obtained in Example 1 were mixed with 1 ml each of buffer solutions, a pH value of 7.3 being 0.2 M phosphate buffer, pH values of 9 and 10 being 0.2 M glucine NaCl-NaOH buffer. Following the procedures as in Example 3, the extract was stored for one week and the residual activity was determined.

The results are illustrated in FIG. 2.

EXAMPLE 5

Each 50 ml of aqueous glucose isomerase extracts prepared from "GLUCOSE ISOMERASE NAGASE" and having a pH value of 7.5 and an activity of 198 U/ml were mixed with aqueous ammonia, magnesium hydroxide and sodium hydroxide to adjust the pH values as given in Table 4.

From the respective portion, each 5 ml samples were poured to test tubes which were then sealed and stored at 30° C with shaking for predetermined periods given in Table 4. The pH change, the microbial contamination and the activity were measured.

The results are given in Table 4.

From the results, it is clear that, when the aqueous glucose isomerase extract is stored at a pH ranging from 10 to 11 for thirty days, the residual activities are from 75 to 84% in the case of sodium hydroxide and from 94 to 96% in the case of aqueous ammonia, respectively, and the pH values do not significantly lower.

Table 4

| Additive | pH | | | | Microbial contamination | | | | Activity (U/ml) | | | |
|---|---|---|---|---|---|---|---|---|---|---|---|---|
| | 0 day | 7 days | 14 days | 30 days | 0 day | 7 days | 14 days | 30 days | 0 day | 7 days | 14 days | 30 days |
| None | 7.5 | 7.0 | 6.6 | 6.5 | 0 | 3 | 3 | 3 | 196 | 142 | 122 | 73 |
| 2N NaOH | 9.0 | 7.5 | 7.0 | 6.8 | 0 | 2 | 3 | 3 | 192 | 154 | 131 | 83 |
| 2N NaOH | 10.0 | 8.3 | 7.0 | 7.2 | 0 | 1 | 2 | 2 | 192 | 169 | 146 | 144 |
| 2N NaOH | 11.0 | 9.6 | 9.1 | 8.2 | 0 | 0 | 1 | 2 | 190 | 188 | 169 | 160 |
| 28% aq. ammonia | 10.5 | 10.5 | 10.4 | 10.1 | 0 | 0 | 0 | 0 | 197 | 191 | 185 | 190 |
| 28% aq. ammonia | 10.7 | 10.6 | 10.6 | 10.5 | 0 | 0 | 0 | 0 | 199 | 195 | 195 | 191 |
| Mg(OH)$_2$ * | 10.5 | 7.0 | 7.0 | — | 0 | 1 | 2 | — | 190 | 169 | 154 | — |
| 28% aq. ammonia + 2N NaOH ** | 10.5 | 9.0 | 8.1 | — | 0 | 1 | 1 | — | 195 | 194 | 176 | — |
| 28% aq. ammonia + 2 Mg(OH)$_2$ *** | 10.5 | 10.5 | — | — | 0 | 0 | — | — | 197 | 189 | — | — |

* The concentration of Mg(OH)$_2$ was made to $10^{-4}$ M and then the pH value was adjusted to 10.5 with 2N NaOH.
** The concentration of aqueous ammonia was made to 0.05 M and then the pH value was adjusted to 10.5 with 2N NaOH.
*** The concentration of Mg(OH) was made to $10^{-4}$ M and then the pH value was adjusted to 10.5 with 28% aqueous ammonia.

What is claimed is:

1. A method for preservation of an aqueous glucose isomerase solution comprising adjusting the pH value of the aqueous solution to a range of from 9 to 12, wherein said aqueous solution is stored for a period of not less than three days.

2. A method for preservation of an aqueous glucose isomerase solution according to claim 1, wherein said pH value is adjusted with at least one alkaline material of sodium hydroxide, potassium hydroxide and magnesium hydroxide.

3. A method of preservation of an aqueous glucose isomerase solution according to claim 1, wherein said pH value is adjusted with sodium hydroxide.

4. A method for preservation of an aqueous glucose isomerase solution according to claim 1, wherein said pH value is adjusted with potassium hydroxide.

5. A method for preservation of an aqueous glucose isomerase solution according to claim 1, wherein said pH value is adjusted with magnesium hydroxide.

6. A method for preservation of an aqueous glucose isomerase solution according to claim 1, wherein said pH value is adjusted with ammonium hydroxide in combination with at least one alkaline material of sodium hydroxide, potassium hydroxide and magnesium hydroxide.

7. A method for preservation of an aqueous glucose isomerase solution according to claim 1, wherein said pH value is within a range of from 10 to 11.

8. A method for preservation of an aqueous glucose isomerase solution according to claim 1, wherein said pH value is adjusted within a range of from 10 to 11 with ammonium hydroxide.

9. A method for preservation of an aqueous glucose isomerase solution according to claim 1, wherein said aqueous solution is stored for a period not less than seven days.

10. A method for preservation of an aqueous glucose isomerase solution according to claim 1, wherein said aqueous solution is stored for a period not less than thirty days.

* * * * *